(12) United States Patent
Koga et al.

(10) Patent No.: US 12,220,547 B2
(45) Date of Patent: Feb. 11, 2025

(54) BALLOON CATHETER

(71) Applicant: KANEKA CORPORATION, Osaka (JP)

(72) Inventors: Yojiro Koga, Settsu (JP); Masahiro Kojima, Settsu (JP); Yoshinori Nakano, Settsu (JP); Masato Tsueda, Settsu (JP); Shintaro Osumi, Settsu (JP)

(73) Assignee: KANEKA CORPORATION, Osaka (JP)

( * ) Notice: Subject to any disclaimer, the term of this patent is extended or adjusted under 35 U.S.C. 154(b) by 716 days.

(21) Appl. No.: 17/442,436

(22) PCT Filed: Mar. 6, 2020

(86) PCT No.: PCT/JP2020/009620
§ 371 (c)(1),
(2) Date: Sep. 23, 2021

(87) PCT Pub. No.: WO2020/195697
PCT Pub. Date: Oct. 1, 2020

(65) Prior Publication Data
US 2022/0184353 A1 Jun. 16, 2022

(30) Foreign Application Priority Data
Mar. 28, 2019 (JP) ................................ 2019-063580

(51) Int. Cl.
*A61M 25/10* (2013.01)
(52) U.S. Cl.
CPC ...... *A61M 25/104* (2013.01); *A61M 25/1002* (2013.01); *A61M 2025/1004* (2013.01);
(Continued)

(58) Field of Classification Search
CPC ............ A61M 25/104; A61M 25/1002; A61M 2025/1004; A61M 2025/1081; A61M 2025/109; A61M 2025/1086
See application file for complete search history.

(56) References Cited

U.S. PATENT DOCUMENTS 5,147,302 A * 9/1992 Euteneuer ......... A61M 25/1038
606/191
5,196,024 A 3/1993 Barath
(Continued)

FOREIGN PATENT DOCUMENTS

CN 104971422 A 10/2015
CN 106390288 A 2/2017
(Continued)

OTHER PUBLICATIONS

International Search Report for PCT/JP2020/009620 mailed on Apr. 21, 2020.
(Continued)

*Primary Examiner* — Katherine M Rodjom
(74) *Attorney, Agent, or Firm* — Birch, Stewart, Kolasch & Birch, LLP

(57) ABSTRACT

Provided is a balloon catheter wherein a balloon is less likely to swell in the protective tube during an air leak test of the balloon in a state where the balloon having projecting portions is housed in a lumen of the protective tube. A balloon catheter contains: a shaft extending in a distal-proximal direction; a balloon having wing-shaped portions; projecting portions disposed on an outer surface of the balloon; and a protective tube in which the balloon is disposed, wherein, in a cross section perpendicular to the distal-proximal direction at a midpoint of a length in the distal-proximal direction of the protective tube, a distance from a centroid of the protective tube through an apex of each projecting portion to an inner surface of the protective (Continued)

tube is longer than a distance from the centroid through none of the projecting portions to the inner surface of the protective tube.

20 Claims, 7 Drawing Sheets

(52) U.S. Cl.
CPC ............... *A61M 2025/1081* (2013.01); *A61M 2025/109* (2013.01)

(56) References Cited

U.S. PATENT DOCUMENTS

| | | | |
|---|---|---|---|
| 5,320,634 A | 6/1994 | Vigil et al. | |
| 6,152,994 A | 11/2000 | Holman et al. | |
| 7,279,002 B2 | 10/2007 | Shaw et al. | |
| 2003/0153870 A1* | 8/2003 | Meyer ................ | A61M 25/104 604/96.01 |
| 2003/0163148 A1 | 8/2003 | Wang et al. | |
| 2004/0034384 A1* | 2/2004 | Fukaya ............... | A61M 25/104 606/191 |
| 2005/0015107 A1 | 1/2005 | O'Brien | |
| 2008/0171977 A1 | 7/2008 | Blix | |
| 2009/0234283 A1 | 9/2009 | Burton et al. | |
| 2011/0099789 A1 | 5/2011 | Ewing et al. | |
| 2011/0301565 A1 | 12/2011 | Weber | |
| 2012/0130407 A1 | 5/2012 | Aggerholm et al. | |
| 2012/0136367 A1 | 5/2012 | Pacetti et al. | |
| 2012/0191111 A1 | 7/2012 | Aggerholm et al. | |
| 2012/0215251 A1 | 8/2012 | Burton et al. | |
| 2013/0150874 A1 | 6/2013 | Kassab | |
| 2015/0150586 A1 | 6/2015 | Aggerholm et al. | |
| 2016/0058982 A1 | 3/2016 | Aggerholm et al. | |
| 2016/0128718 A1 | 5/2016 | Aggerholm et al. | |
| 2017/0112526 A1 | 4/2017 | Burton et al. | |
| 2018/0296241 A1 | 10/2018 | Burton et al. | |
| 2019/0091452 A1* | 3/2019 | Fujisawa ........ | A61B 17/320725 |
| 2021/0113821 A1 | 4/2021 | Okamoto et al. | |

FOREIGN PATENT DOCUMENTS

| | | |
|---|---|---|
| JP | 2005-517474 A | 6/2005 |
| JP | 2005-518842 A | 6/2005 |
| JP | 2007-518448 A | 7/2007 |
| JP | 4345478 B2 | 10/2009 |
| JP | 2011-245114 A | 12/2011 |
| JP | 2014-506140 A | 3/2014 |
| JP | 2015-104671 A | 6/2015 |
| JP | 2015-163219 A | 9/2015 |
| JP | 2016-178969 A | 10/2016 |
| JP | 2016-221313 A | 12/2016 |
| JP | 2017-60616 A | 3/2017 |

OTHER PUBLICATIONS

Written Opinion of the International Searching Authority for PCT/JP2020/009620 (PCT/ISA/237) mailed on Apr. 21, 2020.
International Search Report for International Application No. PCT/JP2020/003893 dated Mar. 17, 2020.

* cited by examiner

[FIG. 1]
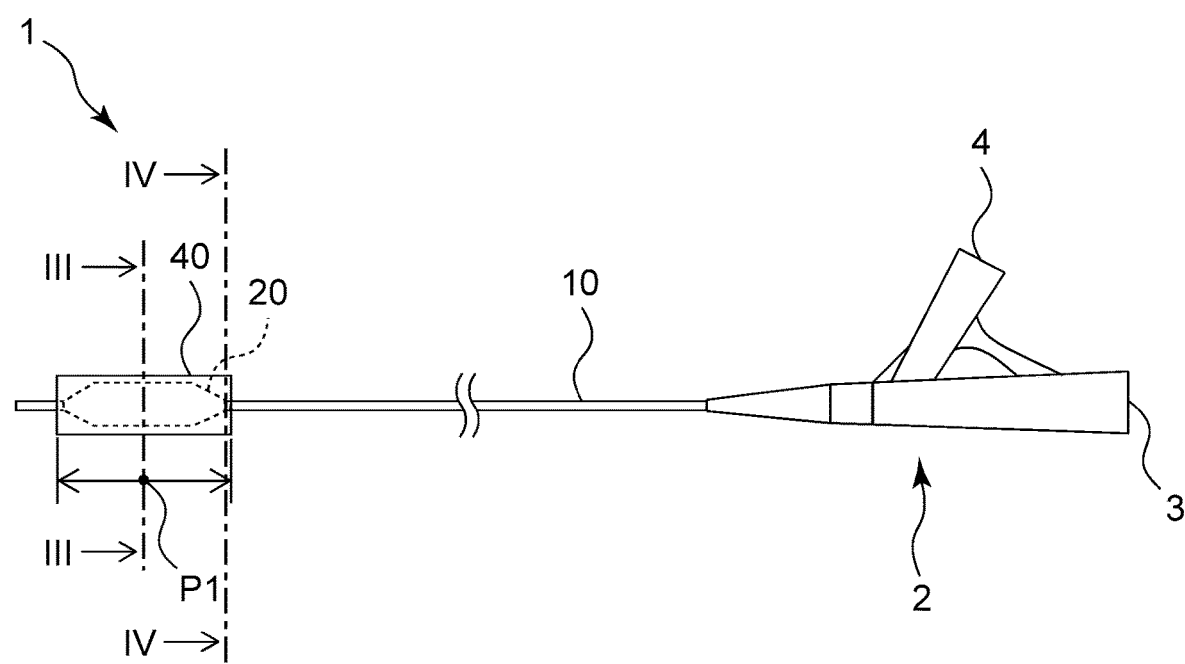

[FIG. 2]
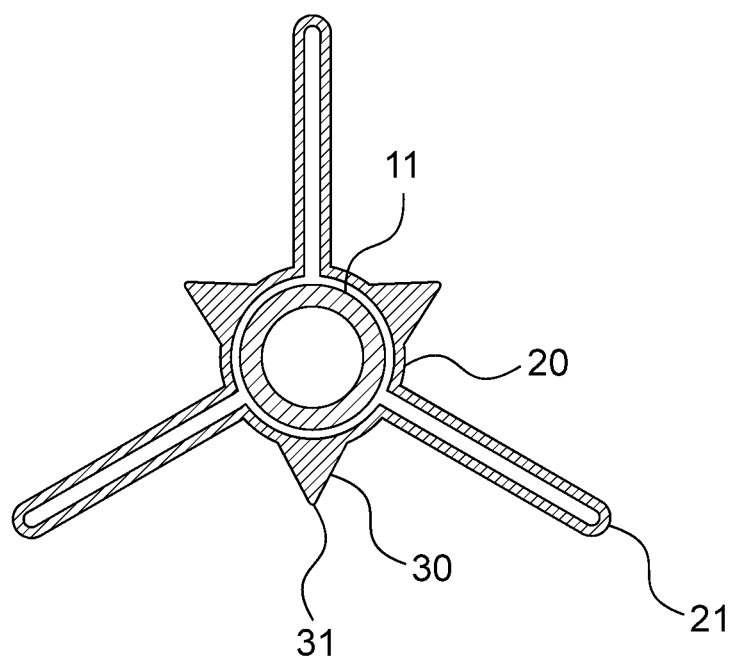

[FIG. 3A]
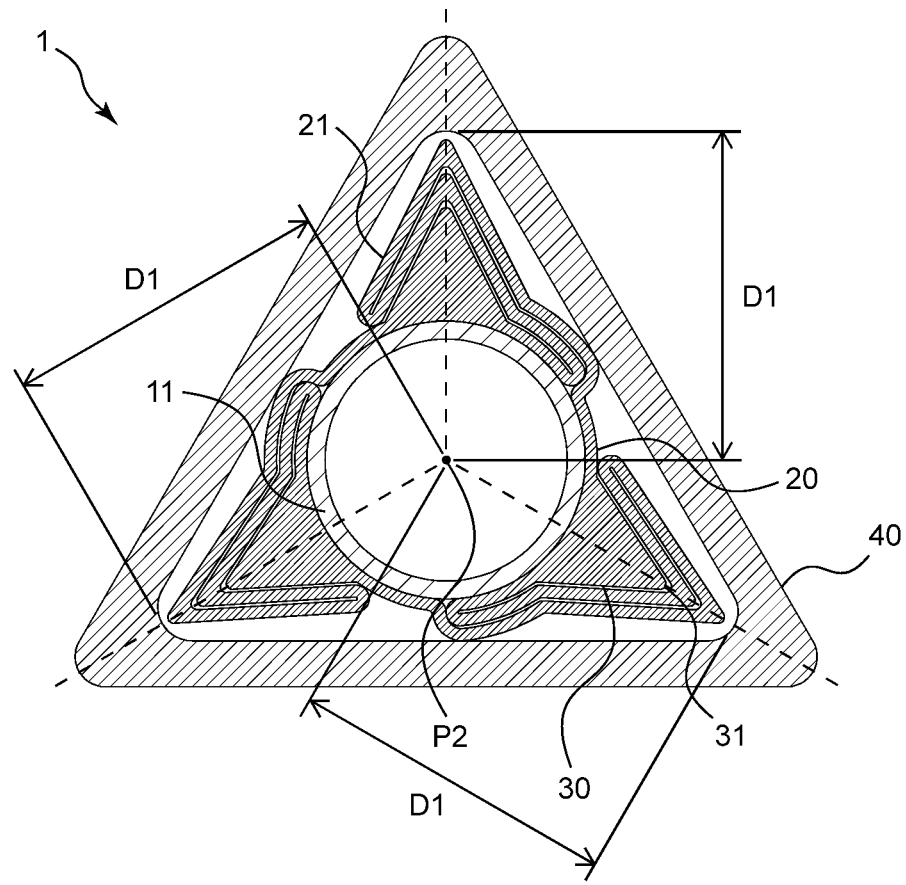
[FIG. 3B]
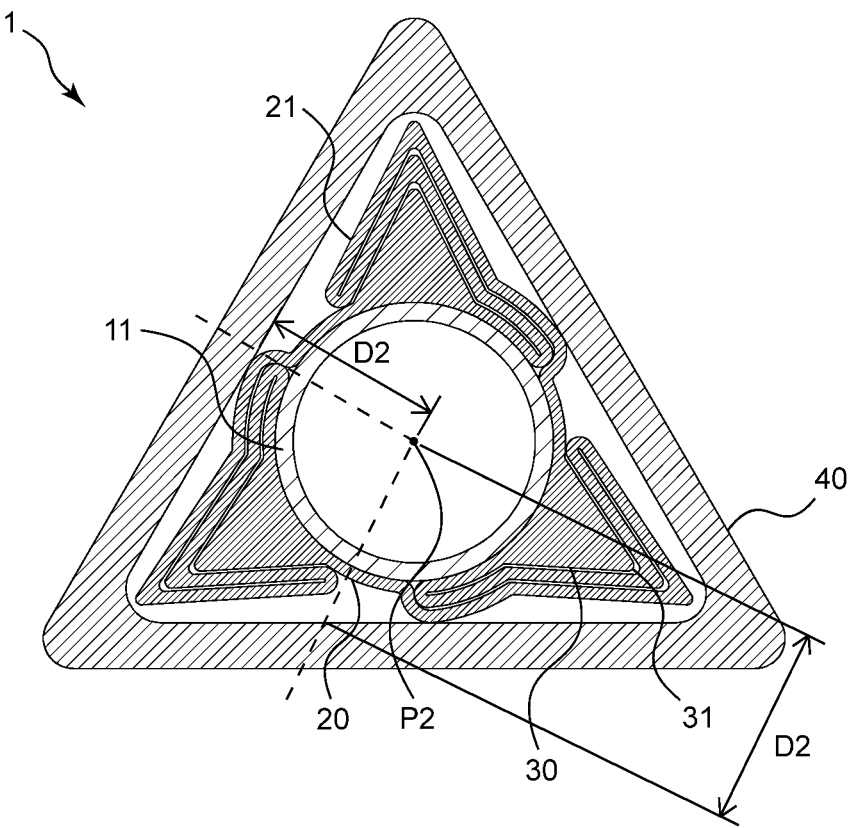

[FIG. 4]
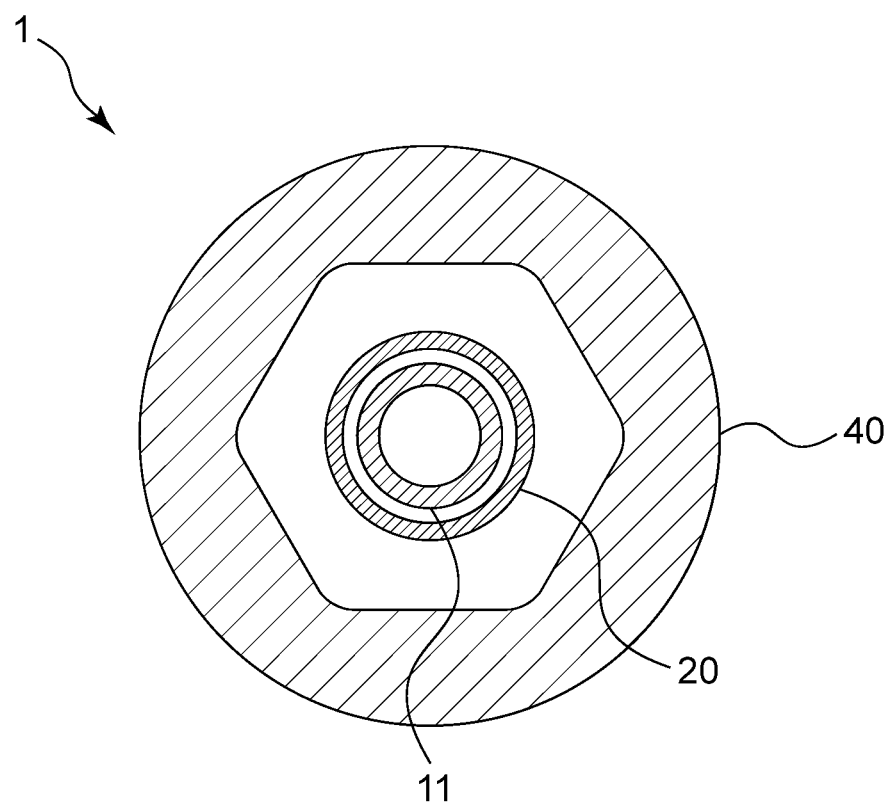

【FIG. 5】
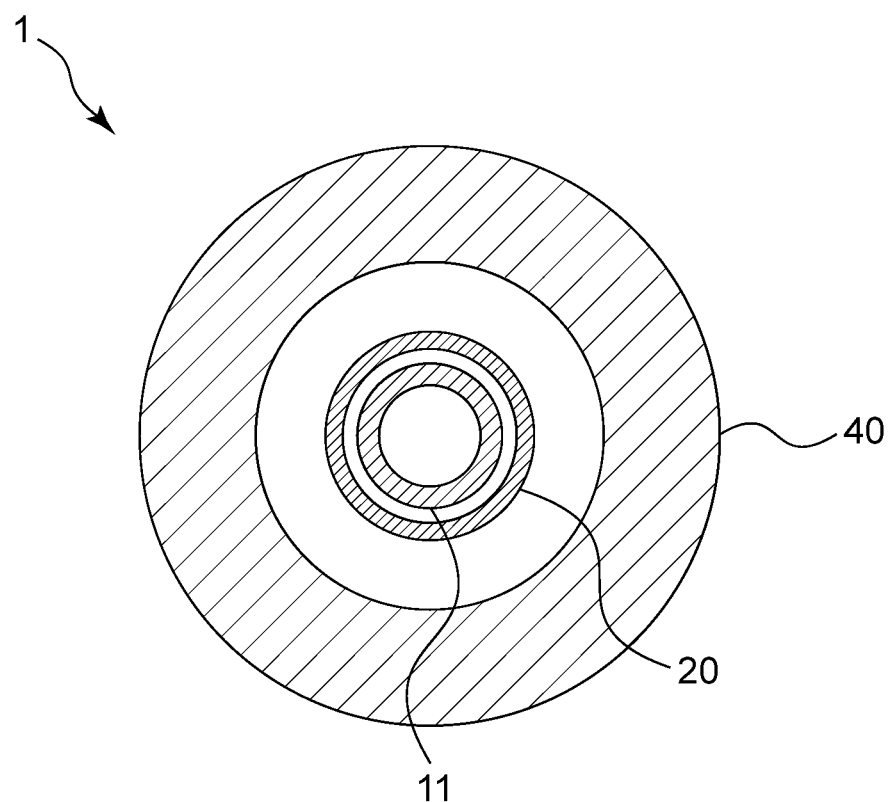

[FIG. 6]
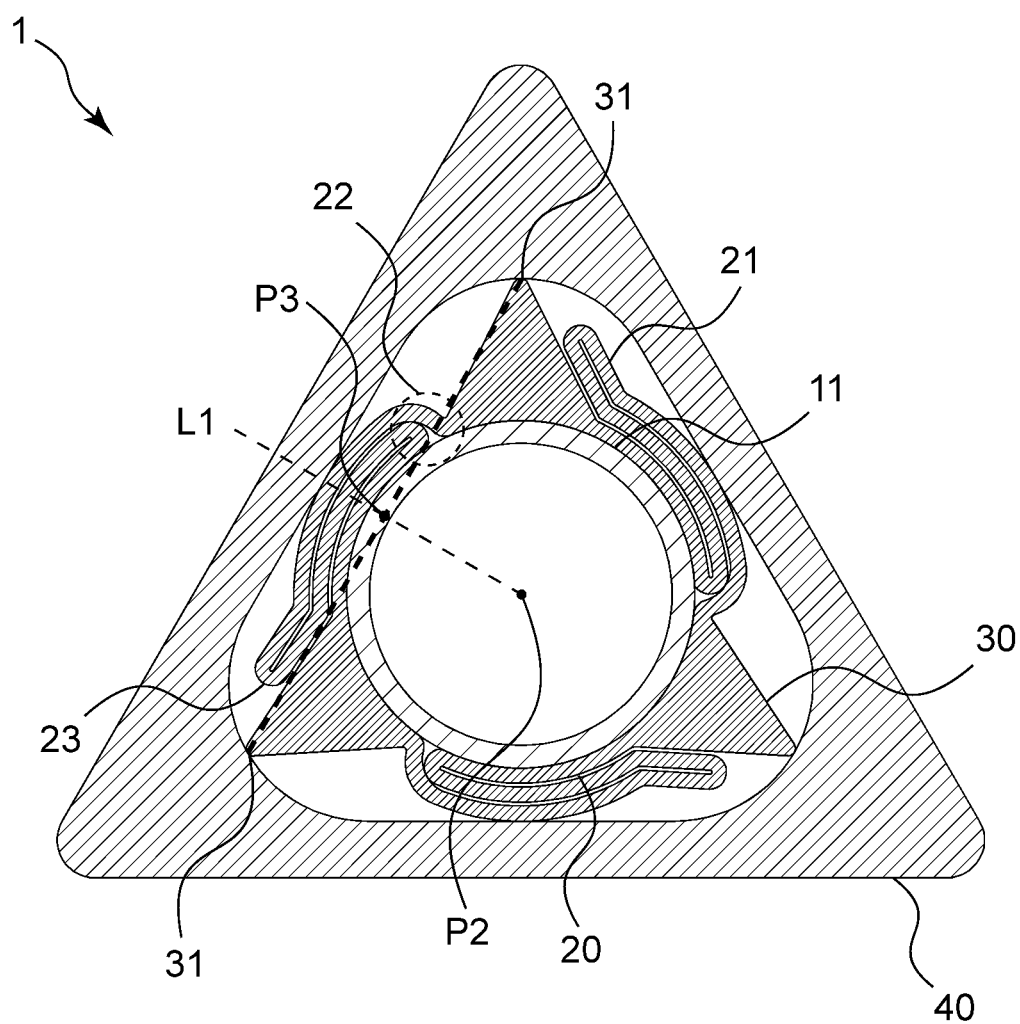

[FIG. 7]
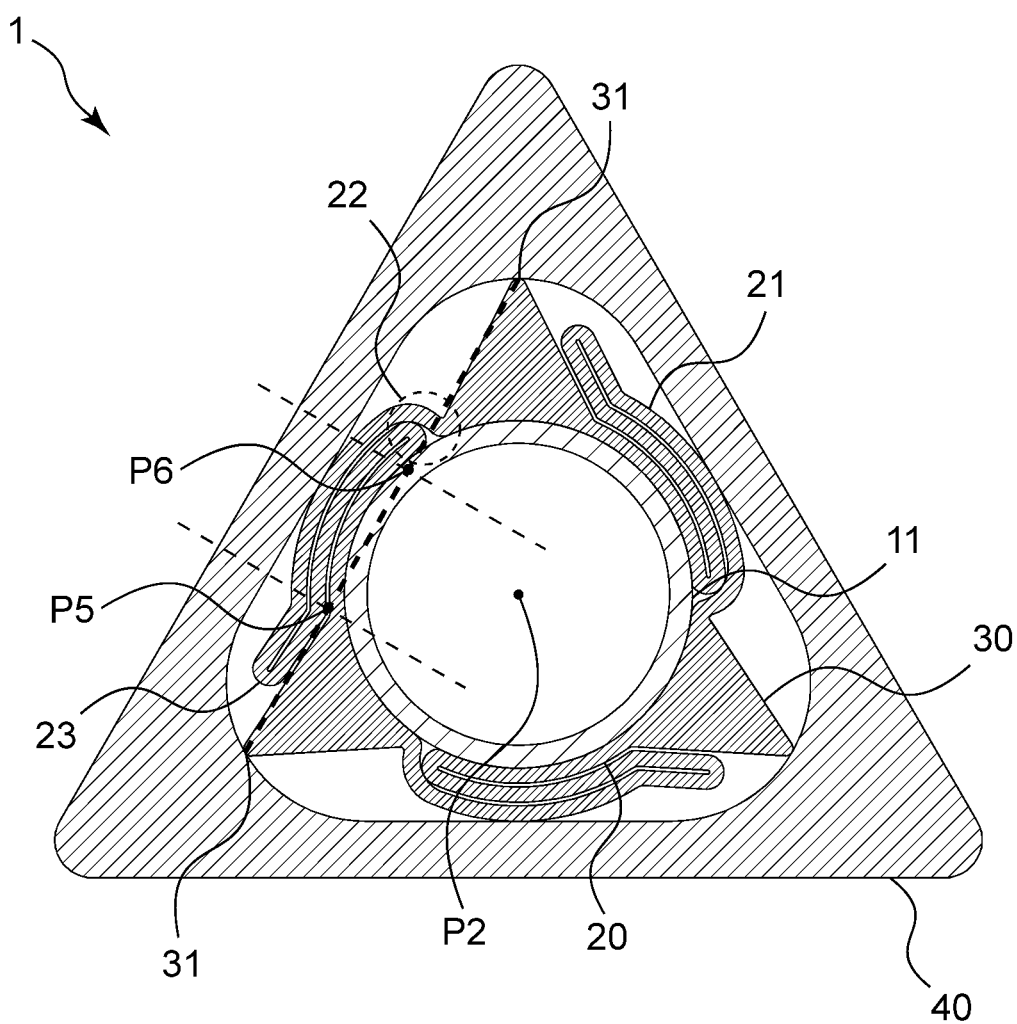

BALLOON CATHETER

TECHNICAL FIELD

The present invention relates to a balloon catheter having a protective tube.

BACKGROUND ART

It has been known that various diseases develop because of stagnation in circulation of blood due to occurrence of a stenosis of a blood vessel which is a flow path for circulating blood in the body. Especially, if a coronary artery for supplying blood to the heart suffers a stenosis, critical diseases such as angina pectoris and myocardial infarction may be caused. As methods for treating such a stenosis site of a blood vessel, there are procedures for expanding the stenosis site by using a balloon catheter, e.g., angioplasties such as PTA and PTCA.

Angioplasties are minimally invasive therapies requiring no thoracotomies such as bypass surgery and are widely conducted.

A stenosis site hardened owing to calcification or the like may be formed on the inner wall of a blood vessel. In the case of such a calcification lesion, it is difficult to expand the hardened stenosis site with a generally used balloon catheter.

Meanwhile, a method is also employed in which a staying and expanding instrument called a stent stays at a stenosis site of a blood vessel, to expand the stenosis site. However, after this treatment, an ISR (In-Stent-Restenosis) lesion may occur in which neointimas in the blood vessel excessively proliferate and a stenosis of the blood vessel occurs again. In the case of the ISR lesion, the neointimas are soft and have slippery surfaces. Thus, with a generally used balloon catheter, the location of the balloon may be shifted from the lesion site at the time of expansion of the balloon, and the blood vessel may be damaged.

As balloon catheters capable of expanding a stenosis site also in the case of such a calcification lesion or ISR lesion, there are balloon catheters in each of which a balloon has a scoring element (for example, Patent Documents 1 to 6).

PRIOR ART DOCUMENTS

Patent Documents

Patent Document 1: JP 2014-506140 A
Patent Document 2: JP 2015-104671 A
Patent Document 3: JP 2015-163219 A
Patent Document 4: JP 2016-221313 A
Patent Document 5: JP 2007-518448 A
Patent Document 6: JP 2005-518842 A

SUMMARY OF INVENTION

Problems to be Solved by the Invention

Ordinarily, a balloon catheter has a form in which a folded balloon is covered by a protective tube formed of a cylindrical tube having an inner diameter slightly larger than the outer diameter of the folded balloon in order to protect the folded balloon until the balloon is used. Also in the balloon catheter having the scoring element in each of Patent Documents 1 to 6, the balloon is considered to be covered by a protective tube in the same manner. However, in this case, the following problem has been found to arise. That is, a gap between the balloon and the protective tube is large, and thus the balloon swells inside the protective tube during an air leak test of the balloon performed before a shipping inspection of the balloon as a product. Consequently, when the balloon is taken out from the protective tube at the time of use of the balloon catheter, the balloon easily expands to have a larger outer diameter, whereby ease of passage of the balloon catheter in a blood vessel deteriorates. In addition, the following problem has also been found to arise. That is, if the inner diameter of the protective tube is made small to reduce the gap between the balloon and the protective tube, it becomes difficult to house the balloon in a lumen of the protective tube, and the balloon or the scoring element is damaged.

The present invention has been made in view of the aforementioned circumstances, and an object of the present invention is to provide a balloon catheter in which: a gap between a balloon having projecting portions and a protective tube is small in a state where the balloon is housed in a lumen of the protective tube; the balloon is less likely to swell in the protective tube during an air leak test of the balloon; and the balloon is easily housed in the lumen of the protective tube.

Solutions to the Problems

A balloon catheter of the present invention that has solved the above problems comprising: a shaft extending in a distal-proximal direction; a balloon disposed on a distal side of the shaft and having, in a contracted state, a plurality of wing-shaped portions; projecting portions disposed on an outer surface of the balloon; and a protective tube having a lumen in which the balloon is disposed, wherein, in a cross section perpendicular to the distal-proximal direction at a midpoint of a length in the distal-proximal direction of the protective tube, a distance from a centroid of the protective tube through an apex of each projecting portion to an inner surface of the protective tube is longer than a distance from the centroid of the protective tube through none of the projecting portions to the inner surface of the protective tube in an interval between the projecting portion and an adjacent projecting portion among the projecting portions.

The balloon catheter is preferable wherein in the cross section perpendicular to the distal-proximal direction at the midpoint of the length in the distal-proximal direction of the protective tube, the distance from the centroid of the protective tube through the apex of the projecting portion to the inner surface of the protective tube is not smaller than 1.1 times and not larger than 4.0 times the distance from the centroid of the protective tube through none of the projecting portions to the inner surface of the protective tube in the interval between the projecting portion and the adjacent projecting portion.

The balloon catheter is preferable wherein the number of the projecting portions is more than one, a cross-sectional shape, of the lumen of the protective tube, perpendicular to the distal-proximal direction at the midpoint of the length in the distal-proximal direction of the protective tube is a polygon, and the number of corners of the polygon is a multiple of the number of the projecting portions.

The balloon catheter is preferable wherein the number of the corners of the polygon is equal to the number of the projecting portions.

The balloon catheter is preferable wherein the projecting portions are disposed at the corners of the polygon.

The balloon catheter is preferable wherein in the cross section perpendicular to the distal-proximal direction at the midpoint of the length in the distal-proximal direction of the protective tube, an area obtained by subtracting an area of each projecting portion from an area of the balloon is not lower than 20% of an area obtained by subtracting the area of the projecting portion from an area of the lumen of the protective tube.

The balloon catheter is preferable wherein in the cross section perpendicular to the distal-proximal direction at the midpoint of the length in the distal-proximal direction of the protective tube, a proportion of an outer periphery, of the balloon, that is in contact with the inner surface of the protective tube to an entire outer periphery of the balloon is not lower than 20%.

The balloon catheter is preferable wherein further comprising an inner tube which is located in a lumen of the balloon and through which a guide wire is inserted.

The balloon catheter is preferable wherein in the cross section perpendicular to the distal-proximal direction at the midpoint of the length in the distal-proximal direction of the protective tube, an area obtained by subtracting an area of each projecting portion from an area of the balloon is not lower than 20% of an area obtained by subtracting the area of the projecting portion from an area of an interval between the inner surface of the protective tube and an outer surface of the inner tube.

The balloon catheter is preferable wherein the balloon and the projecting portions are made as an integrally molded product.

The balloon catheter is preferable wherein an area of the lumen in a cross section perpendicular to the distal-proximal direction of the protective tube at one end of the protective tube is larger than an area of the lumen in the cross section perpendicular to the distal-proximal direction of the protective tube at the midpoint of the length in the distal-proximal direction of the protective tube.

The balloon catheter is preferable wherein a cross-sectional shape, of the lumen of the protective tube, perpendicular to the distal-proximal direction at each of the midpoint of the length in the distal-proximal direction of the protective tube and one end of the protective tube, is a polygon, and the number of corners of the polygon which is the cross-sectional shape, of the lumen of the protective tube, perpendicular to the distal-proximal direction at the midpoint of the length in the distal-proximal direction of the protective tube, is smaller than the number of corners of the polygon which is the cross-sectional shape, of the lumen of the protective tube, perpendicular to the distal-proximal direction at the one end of the protective tube.

The balloon catheter is preferable wherein a cross-sectional shape, of the lumen of the protective tube, perpendicular to the distal-proximal direction at one end of the protective tube, is a circle or an ellipse.

The balloon catheter is preferable wherein the protective tube includes a transitional portion between the midpoint of the length in the distal-proximal direction of the protective tube and one end of the protective tube, and the transitional portion is such that a shape of the lumen at the transitional portion is helically twisted about the distal-proximal direction.

The balloon catheter is preferable wherein the number of the projecting portions is more than one, and, in the cross section perpendicular to the distal-proximal direction, each wing-shaped portion has an origin located closer to one side relative to a straight line connecting the centroid of the protective tube to a midpoint between the apex of a projecting portion and the apex of a projecting portion adjacent to the projecting portion among the projecting portions.

The balloon catheter is preferable wherein in the cross section perpendicular to the distal-proximal direction, the wing-shaped portion has a tip located closer to another side opposite to the one side.

The balloon catheter is preferable wherein the wing-shaped portions are wound and folded in a circumferential direction of the balloon, and all the wing-shaped portions are folded in one direction of the circumferential direction of the balloon.

The balloon catheter is preferable wherein the projecting portions include a projecting portion that has an apex in contact with a corresponding one of the wing-shaped portions.

The balloon catheter is preferable wherein the projecting portions include a projecting portion that has an apex in contact with the inner surface of the protective tube.

Effects of the Invention

According to the balloon catheter of the present invention, in the cross section perpendicular to the distal-proximal direction at the midpoint of the length in the distal-proximal direction of the protective tube, the distance from the centroid of the protective tube through the apex of each projecting portion to the inner surface of the protective tube is longer than the distance from the centroid of the protective tube through none of the projecting portions to the inner surface of the protective tube in the interval between the projecting portion and an adjacent projecting portion among the projecting portions. Thus, the gap between the protective tube and the balloon can be made small in a state where the balloon is housed in the lumen of the protective tube. Therefore, the balloon is less likely to swell in the protective tube during an air leak test of the balloon, and the balloon having the projecting portions can be easily housed in the lumen of the protective tube.

BRIEF DESCRIPTION OF THE DRAWINGS

FIG. 1 illustrates the entirety of a balloon catheter according to an embodiment of the present invention.

FIG. 2 is a cross-sectional view, perpendicular to a distal-proximal direction, of a balloon in a contracted state in the embodiment of the present invention.

FIGS. 3A and 3B are each a cross-sectional view, at III-III, of the balloon catheter shown in FIG. 1.

FIG. 4 is a cross-sectional view, at IV-IV, of the balloon catheter shown in FIG. 1.

FIG. 5 is a cross-sectional view perpendicular to the distal-proximal direction at one end of a protective tube in another embodiment of the present invention.

FIG. 6 is a cross-sectional view perpendicular to the distal-proximal direction at a midpoint of a length in the distal-proximal direction of the protective tube in still another embodiment of the present invention.

FIG. 7 is a cross-sectional view perpendicular to the distal-proximal direction at the midpoint of the length in the distal-proximal direction of the protective tube in a different embodiment of the present invention.

MODE FOR CARRYING OUT THE INVENTION

Hereinafter, the present invention will be more specifically described based on the following embodiments. However, the present invention is not limited to the following embodiments and, as a matter of course, can also be carried out with appropriate modifications being made within the scope of the gist described above and below, and any of these modifications are included in the technical scope of the present invention. In any of the drawings, hatching, reference characters for members, or the like may be omitted for convenience. In this case, see the description and the other drawings. Since priority is given to facilitating the understanding of the characteristics of the present invention, the dimensions of various members in the drawings may be different from actual dimensions.

FIG. 1 illustrates the entirety of a balloon catheter 1 according to an embodiment of the present invention. FIG. 2 is a cross-sectional view, perpendicular to a distal-proximal direction, of a balloon 20 in a contracted state. As shown in FIG. 1 and FIG. 2, the balloon catheter 1 includes: a shaft 10 extending in a distal-proximal direction; a balloon 20 disposed on a distal side of the shaft 10 and having, in a contracted state, a plurality of wing-shaped portions 21; a projecting portion 30 disposed on an outer surface of the balloon 20; and a protective tube 40 having a lumen in which the balloon 20 is disposed.

In the present invention, the distal side refers to a patient side in the extending direction of the shaft 10, and a proximal side refers to the side opposite to the distal side. That is, the proximal side refers to the hand side of a user, i.e., a surgeon, in the extending direction of the shaft 10. A direction from the proximal side to the distal side of the shaft 10 is referred to as a distal-proximal direction.

FIG. 1 shows a configuration example of a so-called over-the-wire balloon catheter 1 in which a guide wire to guide the balloon catheter 1 to advance is inserted from the distal side to the proximal side of the shaft 10. The present invention is applicable also to a so-called rapid-exchange balloon catheter in which a guide wire is inserted from the distal side halfway to the proximal side of the shaft 10.

The balloon catheter 1 is configured such that a fluid is supplied into the balloon 20 through the shaft 10. Expansion and contraction of the balloon 20 can be controlled by using an indeflator (pressurizer for balloons). The fluid may be a pressure fluid pressurized by a pump or the like.

The shaft 10 extends in the distal-proximal direction and has therein a flow path for a fluid. The shaft 10 preferably also has therein an insertion path for a guide wire. Examples of the configuration in which the shaft 10 has therein the flow path for a fluid and the insertion path for a guide wire, include a configuration in which the shaft 10 has an outer tube and an inner tube, the inner tube functions as the insertion path for a guide wire, and the space between the inner tube and the outer tube functions as the flow path for a fluid. In the case where the shaft 10 has the outer tube and the inner tube, it is preferable that: the inner tube extends from the distal end of the outer tube and penetrates the balloon 20 in the distal-proximal direction; the distal side of the balloon 20 is joined to the inner tube; and the proximal side of the balloon 20 is joined to the outer tube.

The shaft 10 may have, on the proximal side thereof, a hub 2 in order to inject a fluid into the shaft 10. The hub 2 preferably includes: a fluid injection portion 3 in communication with the flow path for a fluid to be supplied into the balloon 20; and a guide wire insertion portion 4 in communication with the insertion path for a guide wire. If the balloon catheter 1 has the hub 2 including the fluid injection portion 3 and the guide wire insertion portion 4, it becomes easy to perform: an operation of expanding the balloon 20 by supplying a fluid into the balloon 20; an operation of contracting the balloon 20 by removing the fluid from inside the balloon 20; and an operation of sending the balloon catheter 1 to a treatment target site along a guide wire.

Examples of the manner of joining together the shaft 10 and the hub 2 include adhesion by means of an adhesive, welding, and the like. In particular, the shaft 10 and the hub 2 are preferably joined together by adhesion. If the shaft 10 and the hub 2 are adhered to each other, in cases where the material of the shaft 10 and the material of the hub 2 are different from each other, e.g., a case where the shaft 10 is made from a material having a high flexibility and the hub 2 is made from a material having a high rigidity, the joining strength between the shaft 10 and the hub 2 can be increased and the durability of the balloon catheter 1 can be increased.

Examples of the material of the shaft 10 include polyamide-based resins, polyester-based resins, polyurethane-based resins, polyolefin-based resins, fluorine-based resins, vinyl chloride-based resins, silicone-based resins, natural rubbers, and the like. Only one type of these materials may be used, or two or more types of these materials may be used in combination. In particular, the material of the shaft 10 is preferably at least one of polyamide-based resins, polyolefin-based resins, and fluorine-based resins. If the material of the shaft 10 is at least one of polyamide-based resins, polyolefin-based resins, and fluorine-based resins, the slipperiness of the surface of the shaft 10 can be increased. As a result, ease of insertion of the balloon catheter 1 into a blood vessel can be improved.

As shown in FIG. 1, the balloon 20 is disposed on the distal side of the shaft 10. Examples of the manner of joining together the balloon 20 and the shaft 10 include: adhesion by means of an adhesive; welding; a manner in which a ring-shaped member is attached on a portion at which an end portion of the balloon 20 and the shaft 10 are superposed, and crimping is performed; and the like. In particular, the balloon 20 and the shaft 10 are preferably joined together by welding. If the balloon 20 and the shaft 10 are welded to each other, disconnection is less likely to occur at the joint between the balloon 20 and the shaft 10 even by repetitive expansion and contraction of the balloon 20. Thus, the joining strength between the balloon 20 and the shaft 10 can be easily increased.

The balloon 20 preferably includes: a straight tube portion; a proximal-side tapered portion connected to the proximal side of the straight tube portion; and a distal-side tapered portion connected to the distal side of the straight tube portion. The proximal-side tapered portion and the distal-side tapered portion are each preferably formed such that the diameter thereof is reduced toward a side away from the straight tube portion. If the balloon 20 includes the straight tube portion, the straight tube portion is sufficiently brought into contact with a stenosis site, and it becomes easy to expand the stenosis site. In addition, if the balloon 20 includes the proximal-side tapered portion and the distal-side tapered portion each having an outer diameter that is reduced toward the side away from the straight tube portion, the outer diameter of each of a distal end portion and a proximal end portion of the balloon 20 is reduced at the time of contracting the balloon 20 and winding the balloon 20 on the shaft 10. Accordingly, the height difference between the shaft 10 and the balloon 20 can be made small. Therefore, it becomes easy to insert the balloon 20 in the distal-proximal direction. In the present invention, an inflatable portion is regarded as the balloon 20.

Examples of the material of the balloon 20 include: polyolefin-based resins such as polyethylene, polypropylene, and ethylene-propylene copolymer; polyester-based resins such as polyethylene terephthalate and polyester elastomer; polyurethane-based resins such as polyurethane and polyurethane elastomer; polyphenylene sulfide-based resins; polyamide-based resins such as polyamide and polyamide elastomer; vinyl chloride-based resins; fluorine-based resins; silicone-based resins; natural rubbers such as latex rubber; and the like. Only one type of these materials may be used, or two or more types of these materials may be used in combination. In particular, the material of the balloon 20 is preferably a polyamide-based resin and more preferably nylon 12. If the material of the balloon 20 is a polyamide-based resin, the flexibility of the balloon 20 is increased. Thus, when the balloon 20 is contracted and folded, the outer diameter thereof can be made small. Therefore, it becomes easy to dispose the balloon 20 in the lumen of the protective tube 40.

The outer diameter of the balloon 20 is preferably not smaller than 0.5 mm, more preferably not smaller than 1 mm, and further preferably not smaller than 3 mm. If the lower limit value of the outer diameter of the balloon 20 is set to fall within the above range, a stenosis site in a blood vessel can be sufficiently expanded. Meanwhile, the outer diameter of the balloon 20 is preferably not larger than 35 mm, more preferably not larger than 30 mm, and further preferably not larger than 25 mm. If the upper limit value of the outer diameter of the balloon 20 is set to fall within the above range, the outer diameter of the balloon 20 can be prevented from being excessively increased, and it is possible to make a balloon 20 that is easily disposed in the lumen of the protective tube 40.

The length in the distal-proximal direction of the balloon 20 is preferably not smaller than 5 mm, more preferably not smaller than 10 mm, and further preferably not smaller than 15 mm. If the lower limit value of the length in the distal-proximal direction of the balloon 20 is set to fall within the above range, the area of a stenosis site that can be expanded at once can be increased, and the time taken for a procedure can be shortened. Meanwhile, the length in the distal-proximal direction of the balloon 20 is preferably not larger than 300 mm, more preferably not larger than 200 mm, and further preferably not larger than 100 mm. If the upper limit value of the length in the distal-proximal direction of the balloon 20 is set to fall within the above range, the amount of a fluid to be supplied into the balloon 20 to expand a stenosis site can be reduced, and the time required for sufficiently expanding the balloon 20 can be shortened.

The thickness of the balloon 20 is preferably not smaller than 5 µm, more preferably not smaller than 7 µm, and further preferably not smaller than 10 µm. If the lower limit value of the thickness of the balloon 20 is set to fall within the above range, the strength of the balloon 20 can be increased, and a stenosis site can be sufficiently expanded. Meanwhile, the upper limit value of the thickness of the balloon 20 can be set according to use of the balloon catheter 1. For example, in the case of use as a high-pressure-resistant balloon 20, the thickness is preferably 30 µm to 45 µm. Further, in the case of intending to improve ease of passage of a portion around the balloon 20, regarding the upper limit value, the thickness of the balloon 20 is preferably not larger than 30 µm.

As shown in FIG. 2, the balloon 20 has, in a contracted state, the plurality of wing-shaped portions 21. Each wing-shaped portion 21 refers to a portion, of the balloon 20, at which corresponding inner surface portions are in contact with each other in a state where the balloon 20 is contracted.

The projecting portion 30 is disposed on the outer surface of the balloon 20. By expanding the balloon 20 of the balloon catheter 1 in the case of a calcification lesion, the projecting portion 30 cracks the calcified and hardened lesion site, and the balloon 20 can be sufficiently expanded.

In addition, by expanding the balloon 20 of the balloon catheter 1 in the case of an ISR lesion, the projecting portion 30 is caught on a soft neointima having a slippery surface, and the balloon 20 is less likely to be positionally shifted at the time of expansion against the ISR lesion.

The projecting portion 30 may be located on the wing-shaped portion 21. However, the projecting portion 30 is preferably located on a portion other than the wing-shaped portion 21 as shown in FIG. 2. If the projecting portion 30 is located on a portion other than the wing-shaped portion 21, the wing-shaped portion 21 and the projecting portion 30 are disposed at locations that are different from each other in a circumferential direction of the balloon 20 in a contracted state. As a result, when the wing-shaped portion 21 of the balloon 20 is folded, the outer diameter of the balloon 20 can be made small, and it becomes easy to dispose the balloon 20 in the lumen of the protective tube 40.

The number of projecting portions 30 may be one but is preferably more than one. That is, a plurality of projecting portions 30 are preferably disposed on the outer surface of the balloon 20. If the number of the projecting portions 30 is more than one, it becomes easy to crack a lesion site hardened by calcification. In addition, if the number of the projecting portions 30 is more than one, the balloon 20 can be made further less likely to be positionally shifted with respect to the ISR lesion.

If the number of the projecting portions 30 is more than one and the projecting portions 30 are located on portions other than the wing-shaped portions 21, the number of wing-shaped portions 21 disposed between two adjacent projecting portions 30 may be one but is preferably more than one. If a plurality of wing-shaped portions 21 are disposed between the two adjacent projecting portions 30, the length per one wing-shaped portion 21 can be shortened. Therefore, it becomes easy to house the balloon 20 in the lumen of the protective tube 40 in a state where the balloon 20 is contracted and the wing-shaped portions 21 are folded.

Each projecting portion 30 extends in the distal-proximal direction. The length in the distal-proximal direction of the projecting portion 30 is preferably shorter than the length in the distal-proximal direction of the balloon 20. If the length in the distal-proximal direction of the projecting portion 30 is shorter than the length in the distal-proximal direction of the balloon 20, a location at which no projecting portion 30 is disposed is present in a portion in the distal-proximal direction of the balloon 20. Thus, the balloon 20 is easily bent, and ease of insertion of the balloon catheter 1 in a curved blood vessel or the like can be increased.

Examples of the material of the projecting portion 30 include synthetic resins such as: polyvinyl chloride; polyolefin-based resins such as polyethylene, polypropylene, and cyclic polyolefins; polystyrene-based resins; polymethylpentene-based resins such as poly-(4-methylpentene-1); polycarbonate-based resins; acrylic-based resins; ABS-based resins; polyester-based resins such as polyethylene terephthalate and polyethylene naphthalate; butadiene-styrene copolymers; polyamide-based resins such as nylon 6, nylon 6/6, nylon 6/10, and nylon 12; and metals such as stainless steel, aluminum, an aluminum alloy, titanium, a titanium alloy, copper, a copper alloy, tantalum, and a cobalt alloy. Only one type of these materials may be used, or two or more types of these materials may be used in combination.

The material of the projecting portion 30 is preferably the same as the material of the balloon 20. If the material of the projecting portion 30 and the material of the balloon 20 are the same as each other, the projecting portion 30 and the balloon 20 can be joined together by welding or the like. Thus, the joining strength between the projecting portion 30 and the balloon 20 can be increased.

The balloon 20 and the projecting portion 30 are preferably made as an integrally molded product. That is, the balloon 20 having the projecting portion 30 is preferably formed by integral molding. If the balloon 20 and the projecting portion 30 are formed by integral molding, the projecting portion 30 can be firmly joined to the balloon 20.

The height of the projecting portion 30 is preferably higher than the thickness of the balloon 20. If the height of the projecting portion 30 is higher than the thickness of the balloon 20, it becomes easy for the projecting portion 30 to be caught and fixed on a stenosis site also in the case of a calcification lesion or an ISR lesion. The height of the projecting portion 30 refers to a length from the base of the projecting portion 30 and an apex 31 of the projecting portion 30.

The height of the projecting portion 30 is preferably not smaller than 2 times, more preferably not smaller than 3 times, and further preferably not smaller than 5 times the thickness of the balloon 20. If the lower limit value of the ratio of the height of the projecting portion 30 to the thickness of the balloon 20 is set to fall within the above range, it is possible to make a balloon 20 in which the projecting portion 30 is easily caught and fixed on a stenosis site to facilitate expansion of the stenosis site. Meanwhile, the height of the projecting portion 30 is preferably not larger than 100 times, more preferably not larger than 85 times, and further preferably not larger than 70 times the thickness of the balloon 20. If the upper limit value of the ratio of the height of the projecting portion 30 to the thickness of the balloon 20 is set to fall within the above range, the outer diameter of the balloon 20 in a contracted state can be made small. Thus, the gap generated between the balloon 20 and the protective tube 40 in a state where the balloon 20 is housed in the lumen of the protective tube 40, can be made small. Therefore, the balloon 20 can be made less likely to swell in the protective tube 40 during an air leak test of the balloon 20.

As shown in FIG. 1, the protective tube 40 has a lumen in which the balloon 20 is disposed. In order to prevent the projecting portion 30 from being bent, chipped, or otherwise damaged by contact of the projecting portion 30 with another object, the protective tube 40 protects the balloon 20 by covering the balloon 20 until the balloon catheter 1 is used.

Examples of the material of the protective tube 40 include polyamide-based resins, polyester-based resins, polyurethane-based resins, polyolefin-based resins, fluorine-based resins, vinyl chloride-based resins, silicone-based resins, natural rubbers, and the like. Only one type of these materials may be used, or two or more types of these materials may be used in combination. In particular, the material of the protective tube 40 is preferably a polyolefin-based resin. If the material of the protective tube 40 is a polyolefin-based resin, the slidability of a surface of the protective tube 40 is improved, and it becomes easy to dispose the balloon 20 in the lumen of the protective tube 40.

The Shore D hardness of the material of the protective tube 40 is preferably lower than the Shore D hardness of the projecting portion 30. If the Shore D hardness of the material of the protective tube 40 is lower than the Shore D hardness of the material of the projecting portion 30, the projecting portion 30 can be prevented from being flattened, bent, or otherwise damaged even if the inner surface of the protective tube 40 and the projecting portion 30 are brought into contact with each other when the balloon 20 having the projecting portion 30 is disposed in the lumen of the protective tube 40. The Shore D hardness can be measured on the basis of "ISO868: 2003 Plastics and ebonite—Determination of indentation hardness by means of a durometer (Shore hardness)".

The length in the distal-proximal direction of the protective tube 40 is preferably longer than the length in the distal-proximal direction of the balloon 20. If the length in the distal-proximal direction of the protective tube 40 is longer than the length in the distal-proximal direction of the balloon 20, the entire balloon 20 can be housed in the lumen of the protective tube 40. Therefore, the projecting portion 30 can be sufficiently protected.

The length in the distal-proximal direction of the protective tube 40 is preferably not smaller than 1.05 times, more preferably not smaller than 1.1 times, and further preferably not smaller than 1.15 times the length in the distal-proximal direction of the balloon 20. If the lower limit value of the ratio of the length in the distal-proximal direction of the protective tube 40 to the length in the distal-proximal direction of the balloon 20 is set to fall within the above range, the entire balloon 20 can be sufficiently covered by the protective tube 40 and can be protected by the protective tube 40 such that the projecting portion 30 is not exposed. Meanwhile, the length in the distal-proximal direction of the protective tube 40 is preferably not larger than 2 times, more preferably not larger than 1.8 times, and further preferably not larger than 1.6 times the length in the distal-proximal direction of the balloon 20. If the upper limit value of the ratio of the length in the distal-proximal direction of the protective tube 40 to the length in the distal-proximal direction of the balloon 20 is set to fall within the above range, the length in the distal-proximal direction of the protective tube 40 is prevented from becoming excessively long. Thus, it becomes easy to: house the balloon 20 in the lumen of the protective tube 40; and detach the protective tube 40 when the balloon catheter 1 is used.

The thickness of the protective tube 40 is preferably larger than the height of the projecting portion 30. If the thickness of the protective tube 40 is larger than the height of the projecting portion 30, the strength of the protective tube 40 is increased. Thus, even when force is applied to the balloon 20 from outside the protective tube 40, the projecting portion 30 is prevented from being deformed or damaged. Therefore, the projecting portion 30 can be sufficiently protected.

The thickness of the protective tube 40 is preferably not smaller than 1.1 times, more preferably not smaller than 1.2 times, and further preferably not smaller than 1.3 times the height of the projecting portion 30. If the lower limit value of the ratio of the thickness of the protective tube 40 to the height of the projecting portion 30 is set to fall within the above range, the strength of the protective tube 40 is increased. As a result, the protective tube 40 is less likely to be damaged by the projecting portion 30 when the balloon 20 is housed in the lumen of the protective tube 40. Meanwhile, the thickness of the protective tube 40 is preferably not larger than 10 times, more preferably not larger than 8 times, and further preferably not larger than 5 times the height of the projecting portion 30. If the upper limit value of the ratio of the thickness of the protective tube 40 to the height of the projecting portion 30 is set to fall within the above range, the protective tube 40 can be deformed when the projecting portion 30 or the balloon 20 is pressed against the inner surface of the protective tube 40 at the time of housing the balloon 20 in the lumen of the protective tube 40. Therefore, the projecting portion 30 or the balloon 20 and the inner surface of the protective tube 40 can be made less likely to be damaged even when being brought into contact with each other.

FIGS. 3A and 3B are each a cross-sectional view, at III-III, of the balloon catheter 1 shown in FIG. 1. FIGS. 3A and 3B are each a cross-sectional view perpendicular to the distal-proximal direction at a midpoint P1 of the length in the distal-proximal direction of the protective tube 40. As shown in FIGS. 3A and 3B, the balloon 20 in which the plurality of wing-shaped portions 21 are folded in a contracted state is disposed in the lumen of the protective tube 40.

In the cross section perpendicular to the distal-proximal direction at the midpoint P1 of the length in the distal-proximal direction of the protective tube 40, a distance D1 from a centroid P2 of the protective tube 40 through the apex 31 of each projecting portion 30 to the inner surface of the protective tube 40 as shown in FIG. 3A is longer than a distance D2 from the centroid P2 of the protective tube 40 through none of the projecting portions 30 to the inner surface of the protective tube 40 in an interval between the projecting portion 30 and an adjacent projecting portion 30 among the projecting portions 30 as shown in FIG. 3B. The centroid P2 of the protective tube 40 refers to a centroid of the shape of the lumen of the protective tube 40, in the cross section perpendicular to the distal-proximal direction at the midpoint P1 of the length in the distal-proximal direction of the protective tube 40. Since the distance D1 from the centroid P2 of the protective tube 40 through the apex 31 of each projecting portion 30 to the inner surface of the protective tube 40 is longer than the distance D2 from the centroid P2 of the protective tube 40 through none of the projecting portions 30 to the inner surface of the protective tube 40, a space around a portion at which the apex 31 of the projecting portion 30 is located becomes wider than a space around another portion in the lumen of the protective tube 40. Thus, it becomes easy to house the balloon 20 in the lumen of the protective tube 40. In addition, since the distance D1 is longer than the distance D2, the gap between the inner surface of the protective tube 40 and the outer surface of the balloon 20 is made small in a state where the balloon 20 is housed in the lumen of the protective tube 40. Thus, the balloon 20 can be prevented from significantly swelling in the protective tube 40 during an air leak test of the balloon 20.

In the cross section perpendicular to the distal-proximal direction at the midpoint P1 of the length in the distal-proximal direction of the protective tube 40, the distance D1 from the centroid P2 of the protective tube 40 through the apex 31 of each projecting portion 30 to the inner surface of the protective tube 40 is preferably not smaller than 1.1 times and not larger than 4.0 times the distance D2 from the centroid P2 of the protective tube 40 through none of the projecting portions 30 to the inner surface of the protective tube 40 in the interval between the projecting portion 30 and the adjacent projecting portion 30. If the ratio of the distance D1 from the centroid P2 of the protective tube 40 through the apex 31 of each projecting portion 30 to the inner surface of the protective tube 40 to the distance D2 from the centroid P2 of the protective tube 40 through none of the projecting portions 30 to the inner surface of the protective tube 40 is set to fall within the above range, the gap between the inner surface of the protective tube 40 and the outer surface of the balloon 20 can be made small in a state where the balloon 20 is housed in the lumen of the protective tube 40. Therefore, the space in which the balloon 20 swells in the protective tube 40 during an air leak test of the balloon 20 can be made sufficiently small, and the balloon 20 can be made less likely to swell.

In the cross section perpendicular to the distal-proximal direction at the midpoint P1 of the length in the distal-proximal direction of the protective tube 40, the distance D1 from the centroid P2 of the protective tube 40 through the apex 31 of each projecting portion 30 to the inner surface of the protective tube 40 is preferably not smaller than 1.1 times, more preferably not smaller than 1.15 times, further preferably not smaller than 1.2 times, even further preferably not smaller than 1.3 times, particularly preferably not smaller than 1.4 times, and most preferably not smaller than 1.5 times the distance D2 from the centroid P2 of the protective tube 40 through none of the projecting portions 30 to the inner surface of the protective tube 40 in the interval between the projecting portion 30 and the adjacent projecting portion 30. If the lower limit value of the ratio of the distance D1 from the centroid P2 of the protective tube 40 through the apex 31 of the projecting portion 30 to the inner surface of the protective tube 40 to the distance D2 from the centroid P2 of the protective tube 40 through none of the projecting portions 30 to the inner surface of the protective tube 40 is set to fall within the above range, the gap generated between the inner surface of the protective tube 40 and the outer surface of the balloon 20 can be made sufficiently small. Thus, the balloon 20 can be prevented from significantly swelling in the protective tube 40 during an air leak test of the balloon 20.

In addition, in the cross section perpendicular to the distal-proximal direction at the midpoint P1 of the length in the distal-proximal direction of the protective tube 40, the distance D1 from the centroid P2 of the protective tube 40 through the apex 31 of each projecting portion 30 to the inner surface of the protective tube 40 is preferably not larger than 4.0 times, more preferably not larger than 3.9 times, further preferably not larger than 3.8 times, even further preferably not larger than 3.7 times, particularly preferably not larger than 3.6 times, and most preferably not larger than 3.5 times the distance D2 from the centroid P2 of the protective tube 40 through none of the projecting portions 30 to the inner surface of the protective tube 40 in the interval between the projecting portion 30 and the adjacent projecting portion 30. If the upper limit value of the ratio of the distance D1 from the centroid P2 of the protective tube 40 through the apex 31 of the projecting portion 30 to the inner surface of the protective tube 40 to the distance D2 from the centroid P2 of the protective tube 40 through none of the projecting portions 30 to the inner surface of the protective tube 40 is set to fall within the above range, the balloon 20 can be easily housed in the lumen of the protective tube 40.

As shown in FIGS. 3A and 3B, it is preferable that: the number of the projecting portions 30 is more than one; a cross-sectional shape, of the lumen of the protective tube 40, perpendicular to the distal-proximal direction at the midpoint P1 of the length in the distal-proximal direction of the protective tube 40 is a polygon; and the number of corners of the polygon is a multiple of the number of the projecting portions 30. If the cross-sectional shape, of the lumen of the protective tube 40, perpendicular to the distal-proximal direction at the midpoint P1 of the length in the distal-proximal direction of the protective tube 40 is a polygon and the number of corners of the polygon is a multiple of the number of the projecting portions 30, the projecting portions 30 are easily located at the corners of the polygon at the time of disposing the balloon 20 in the lumen of the protective tube 40, and the space in which the balloon 20 swells in the protective tube 40 during an air leak test of the balloon 20 can be reduced by reduction in the gap between the inner surface of the protective tube 40 and the outer surface of the balloon 20.

The polygon in the present invention also encompasses, in addition to a polygon in which the corners have distinct vertices and the sides are straight lines, a so-called round-corner polygon having round corners and a polygon in which the sides are at least partially curved lines. In a case where the polygon has round corners, the radius of each round corner of the polygon is preferably not larger than 3 mm, more preferably not larger than 2 mm, and further preferably not larger than 1 mm. If the upper limit value of the radius of the round corner of the polygon is set to fall within the above range, it becomes easy to dispose the projecting portion 30 at the corner of the polygon, and it becomes easy to house the balloon 20 in the lumen of the protective tube 40.

The number of the corners of the polygon is preferably a multiple of the number of the projecting portions 30 and more preferably equal to the number of the projecting portions 30. If the number of the corners of the polygon is equal to the number of the projecting portions 30, the lumen of the protective tube 40 is made small. As a result, the distance between the inner surface of the protective tube 40 and the outer surface of the balloon 20 is made small when the balloon 20 is disposed in the lumen of the protective tube 40. Thus, the balloon 20 can be made less likely to swell in the protective tube 40 during an air leak test of the balloon 20.

The projecting portions 30 are preferably disposed at the corners of the polygon. If the projecting portions 30 are disposed at the corners of the polygon, the projecting portions 30 having large cross-sectional areas are disposed at the corners at longer distances from the centroid P2 of the protective tube 40 than the other portions, in the cross section perpendicular to the distal-proximal direction of the protective tube 40 at the midpoint P1 of the length in the distal-proximal direction of the protective tube 40. Therefore, it becomes easy to dispose the balloon 20 having the projecting portions 30 in the lumen of the protective tube 40.

Although not shown, in the cross section perpendicular to the distal-proximal direction of the protective tube 40 at the midpoint P1 of the length in the distal-proximal direction of the protective tube 40, the vertex of each corner of the polygon is preferably located on the straight line passing through the centroid P2 of the protective tube 40 and the apex 31 of the corresponding projecting portion 30. If the vertex of the corner of the polygon is located on the straight line passing through the centroid P2 of the protective tube 40 and the apex 31 of the projecting portion 30, the apex 31 at which the projecting portion 30 has the highest height is located at a portion that is at the longest distance from the centroid P2 of the protective tube 40 in the corner. As a result, even if the area of the cross-sectional shape of the lumen of the protective tube 40 is made small in order to reduce the gap between the protective tube 40 and the balloon 20, the balloon 20 having the projecting portion 30 can be easily inserted into the lumen of the protective tube 40.

In the cross section perpendicular to the distal-proximal direction at the midpoint P1 of the length in the distal-proximal direction of the protective tube 40, an area obtained by subtracting the area of each projecting portion 30 from the area of the balloon 20 is preferably not lower than 20% of an area obtained by subtracting the area of the projecting portion 30 from the area of the lumen of the protective tube 40. If the area obtained by subtracting the area of the projecting portion 30 from the area of the balloon 20 is not lower than 20% of the area obtained by subtracting the area of the projecting portion 30 from the area of the lumen of the protective tube 40, the gap generated between the inner surface of the protective tube 40 and the outer surface of the balloon 20 in a state where the balloon 20 having the projecting portion 30 is disposed in the lumen of the protective tube 40, can be made small. Therefore, the balloon 20 can be made less likely to swell in the protective tube 40 during an air leak test of the balloon 20.

In the cross section perpendicular to the distal-proximal direction at the midpoint P1 of the length in the distal-proximal direction of the protective tube 40, the area obtained by subtracting the area of the projecting portion 30 from the area of the balloon 20 is preferably not lower than 20%, more preferably not lower than 25%, and further preferably not lower than 30% of the area obtained by subtracting the area of the projecting portion 30 from the area of the lumen of the protective tube 40. If the lower limit value of the proportion of the area obtained by subtracting the area of the projecting portion 30 from the area of the balloon 20 to the area obtained by subtracting the area of the projecting portion 30 from the area of the lumen of the protective tube 40 is set to fall within the above range, the proportion of a portion obtained by excluding the projecting portion 30 from the balloon 20 to a space having the area obtained by subtracting the area of the projecting portion 30 from the area of the lumen of the protective tube 40, is increased. Thus, the gap generated between the protective tube 40 and the balloon 20 is reduced. Therefore, the balloon 20 can be prevented from significantly swelling in the protective tube 40 during an air leak test of the balloon 20. Meanwhile, in the cross section perpendicular to the distal-proximal direction at the midpoint P1 of the length in the distal-proximal direction of the protective tube 40, the upper limit value of the proportion of the area obtained by subtracting the area of the projecting portion 30 from the area of the balloon 20 to the area obtained by subtracting the area of the projecting portion 30 from the area of the lumen of the protective tube 40, is not particularly limited, and the proportion can be set to be, for example, not higher than 80%, not higher than 70%, or not higher than 60%.

In the cross section perpendicular to the distal-proximal direction at the midpoint P1 of the length in the distal-proximal direction of the protective tube 40, the proportion of an outer periphery, of the balloon 20, that is in contact with the inner surface of the protective tube 40 to the entire outer periphery of the balloon 20 is preferably not lower than 20%. If the proportion of the outer periphery, of the balloon 20, that is in contact with the inner surface of the protective tube 40 to the entire outer periphery of the balloon 20 is not lower than 20%, the balloon 20 is disposed in the lumen of the protective tube 40 in a state where there is a small gap between the inner surface of the protective tube 40 and the outer surface of the balloon 20. Therefore, the gap generated between the balloon 20 and the protective tube 40 can be reduced, and the balloon 20 can be made less likely to swell in the protective tube 40 during an air leak test of the balloon 20.

In the cross section perpendicular to the distal-proximal direction at the midpoint P1 of the length in the distal-proximal direction of the protective tube 40, the proportion of the outer periphery, of the balloon 20, that is in contact with the inner surface of the protective tube 40 to the entire outer periphery of the balloon 20 is preferably not lower than 20%, more preferably not lower than 25%, and further preferably not lower than 30%. If the lower limit value of the proportion of the outer periphery, of the balloon 20, that is in contact with the inner surface of the protective tube 40 to the entire outer periphery of the balloon 20 is set to fall within the above range, the balloon 20 is disposed in the lumen of the protective tube 40 in a state of being more in contact with the inner surface of the protective tube 40. Thus, the gap generated between the outer surface of the balloon 20 and the inner surface of the protective tube 40 can be reduced, and the balloon 20 can be prevented from significantly swelling in the protective tube 40 during an air leak test of the balloon 20. Meanwhile, the upper limit value of the proportion of the outer periphery, of the balloon 20, that is in contact with the inner surface of the protective tube 40 to the entire outer periphery of the balloon 20 is not particularly limited, and the proportion can be set to be, for example, not higher than 50%, not higher than 45%, or not higher than 40%.

As shown in FIGS. 3A and 3B, the balloon catheter 1 preferably further includes an inner tube 11 which is located in the lumen of the balloon 20 and through which a guide wire is inserted. If the inner tube 11 is included in the lumen of the balloon 20, it becomes easy to insert a guide wire through the balloon catheter 1. In addition, if the inner tube 11 is included in the lumen of the balloon 20, a guide wire is inserted through the inner tube 11, and thus the guide wire can be prevented from coming into contact with the balloon 20, whereby the balloon 20 can be prevented from being damaged.

A conventional balloon catheter including an inner tube has the following disadvantages. That is, if there is no sufficient gap between the inner surface of a protective tube and the outer surface of a balloon when the balloon catheter including a projecting portion is housed in the protective tube, the projecting portion of the balloon is pushed to the inner side of the balloon by the protective tube, and the inner tube is squeezed. Consequently, the space through which a guide wire passes is narrowed. Thus, the slidability of the guide wire may be reduced, and it may become impossible to cause the guide wire to pass through the inside of the inner tube (the guide wire is stuck).

Meanwhile, the protective tube 40 has the following advantages. That is, in the cross section perpendicular to the distal-proximal direction at the midpoint P1 of the length in the distal-proximal direction of the protective tube 40, the distance D1 from the centroid P2 of the protective tube 40 through the apex 31 of each projecting portion 30 to the inner surface of the protective tube 40 is longer than the distance D2 from the centroid P2 of the protective tube 40 through none of the projecting portions 30 to the inner surface of the protective tube 40 in the interval between the projecting portion 30 and the adjacent projecting portion 30, whereby the projecting portion 30 is less likely to squeeze the inner tube 11, the reduction in the slidability of a guide wire in the inner tube 11 can be prevented, and the guide wire can be prevented from being stuck.

In a case where the shaft 10 includes an outer tube and an inner tube, the inner tube 11 and the inner tube are preferably integrated with each other. If the inner tube 11 and the inner tube are integrated with each other, a guide wire is easily inserted through the balloon catheter 1, and it becomes easy to move the balloon catheter 1 in the distal-proximal direction along the guide wire. Examples of the manner of integrating the inner tube 11 and the inner tube with each other include: a manner in which the proximal end of the inner tube 11 and the distal end of the inner tube are joined together; a manner in which a single tube member serving both as the inner tube 11 and the inner tube is used; and the like.

Examples of the material of the inner tube 11 include polyamide-based resins, polyester-based resins, polyurethane-based resins, polyolefin-based resins, fluorine-based resins, vinyl chloride-based resins, silicone-based resins, natural rubbers, and the like. Only one type of these materials may be used, or two or more types of these materials may be used in combination. In particular, the material of the inner tube 11 is preferably at least one of polyamide-based resins, polyolefin-based resins, and fluorine-based resins. If the material of the inner tube 11 is at least one of polyamide-based resins, polyolefin-based resins, and fluorine-based resins, the slidability between the inner tube 11 and a guide wire is increased, and it is possible to make a balloon catheter 1 that is easily moved in the distal-proximal direction along the guide wire.

Examples of the shape of a lumen of the inner tube 11 in a cross section perpendicular to the distal-proximal direction of the inner tube 11, include a circle, an ellipse, a polygon, and the like. In particular, as shown in FIGS. 3A and 3B, the shape of the lumen of the inner tube 11 in the cross section perpendicular to the distal-proximal direction of the inner tube 11 is preferably a circle. If the cross-sectional shape of the lumen of the inner tube 11 is a circle, the slidability of the inner surface of the inner tube 11 is increased, and it becomes easy for a guide wire disposed in the lumen of the inner tube 11 to be smoothly moved in the distal-proximal direction in the inner tube 11.

Although the thickness of the inner tube 11 may be smaller than the thickness of the balloon 20 or equal to the thickness of the balloon 20, the thickness of the inner tube 11 is preferably larger than the thickness of the balloon 20. If the thickness of the inner tube 11 is larger than the thickness of the balloon 20, the rigidity of the inner tube 11 can be increased. Therefore, even if the inner surface of the protective tube 40 and the outer surface of the balloon 20 are in contact with each other and force is being applied to the balloon 20, the inner tube 11 is less likely to be deformed. Thus, ease of insertion of a guide wire through the inner tube 11 can be increased.

The thickness of the inner tube 11 is preferably not smaller than 1.05 times, more preferably not smaller than 1.1 times, and further preferably not smaller than 1.15 times the thickness of the balloon 20. If the lower limit value of the ratio of the thickness of the inner tube 11 to the thickness of the balloon 20 is set to fall within the above range, it is possible to make an inner tube 11 that has a high strength and that is less likely to be damaged even when coming into contact with a guide wire. Meanwhile, the thickness of the inner tube 11 is preferably not larger than 5 times, more preferably not larger than 4 times, and further preferably not larger than 3 times the thickness of the balloon 20. If the upper limit value of the ratio of the thickness of the inner tube 11 to the thickness of the balloon 20 is set to fall within the above range, the rigidity of the inner tube 11 is prevented from becoming excessively high. Thus, the inner tube 11 is also curved according to a curved blood vessel or the like, whereby ease of insertion of the balloon catheter 1 can be improved.

The thickness of the inner tube 11 is preferably smaller than the thickness of the protective tube 40. If the thickness of the inner tube 11 is smaller than the thickness of the protective tube 40, when the balloon catheter 1 is disposed in a curved blood vessel or the like, the inner tube 11 can also be curved, and it is possible to make a balloon catheter 1 having a favorable ease of insertion.

The thickness of the inner tube 11 is preferably not higher than 50%, more preferably not higher than 40%, and further preferably not higher than 30% of the thickness of the protective tube 40. If the upper limit value between the thickness of the inner tube 11 and the thickness of the protective tube 40 is set to fall within the above range, the inner tube 11 has a moderate rigidity, and the balloon catheter 1 can be easily inserted also through a curved blood vessel or the like. Meanwhile, the thickness of the inner tube 11 is preferably not lower than 5%, more preferably not lower than 7%, and further preferably not lower than 10% of the thickness of the protective tube 40. If the lower limit value between the thickness of the inner tube 11 and the thickness of the protective tube 40 is set to fall within the above range, even when the inner surface of the protective tube 40 is in a state of being in contact with the outer surface of the balloon 20 and force is applied to the inner tube 11 through the balloon 20, the inner tube 11 is less likely to be deformed and a guide wire can be smoothly inserted into the inner tube 11.

In the cross section perpendicular to the distal-proximal direction at the midpoint P1 of the length in the distal-proximal direction of the protective tube 40, the area obtained by subtracting the area of each projecting portion 30 from the area of the balloon 20 is preferably not lower than 20% of an area obtained by subtracting the area of the projecting portion 30 from the area of an interval between the inner surface of the protective tube 40 and the outer surface of the inner tube 11. If the area obtained by subtracting the area of the projecting portion 30 from the area of the balloon 20 is not lower than 20% of the area obtained by subtracting the area of the projecting portion 30 from the area of the interval between the inner surface of the protective tube 40 and the outer surface of the inner tube 11, a large gap is less likely to be generated between the inner surface of the protective tube 40 and the outer surface of the inner tube 11 when the balloon 20 which has the projecting portion 30 and in which the inner tube 11 is disposed in the lumen is disposed in the lumen of the protective tube 40. As a result, the balloon 20 can be made less likely to swell in the protective tube 40 at the time of performing an air leak test of the balloon 20.

In the cross section perpendicular to the distal-proximal direction at the midpoint P1 of the length in the distal-proximal direction of the protective tube 40, the area obtained by subtracting the area of each projecting portion 30 from the area of the balloon 20 is preferably not lower than 20%, more preferably not lower than 25%, and further preferably not lower than 30% of the area obtained by subtracting the area of the projecting portion 30 from the area of the interval between the inner surface of the protective tube 40 and the outer surface of the inner tube 11. If the lower limit value of the proportion of the area obtained by subtracting the area of the projecting portion 30 from the area of the balloon 20 to the area obtained by subtracting the area of the projecting portion 30 from the area of the interval between the inner surface of the protective tube 40 and the outer surface of the inner tube 11 is set to fall within the above range, the proportion of the portion obtained by excluding the projecting portion 30 from the balloon 20 to the space between the inner surface of the protective tube 40 and the outer surface of the inner tube 11, is increased. Thus, a gap generated between the protective tube 40 and the balloon 20 is reduced. Therefore, the balloon 20 can be prevented from significantly swelling in the protective tube 40 during an air leak test of the balloon 20. Meanwhile, in the cross section perpendicular to the distal-proximal direction at the midpoint P1 of the length in the distal-proximal direction of the protective tube 40, the upper limit value of the proportion of the area obtained by subtracting the area of the projecting portion 30 from the area of the balloon 20 to the area obtained by subtracting the area of the projecting portion 30 from the area of the interval between the inner surface of the protective tube 40 and the outer surface of the inner tube 11 is not particularly limited, and the proportion can be set to be, for example, not higher than 80%, not higher than 70%, or not higher than 60%.

The area of the lumen in a cross section perpendicular to the distal-proximal direction of the protective tube 40 at one end of the protective tube 40 is preferably larger than the area of the lumen in the cross section perpendicular to the distal-proximal direction of the protective tube 40 at the midpoint P1 of the length in the distal-proximal direction of the protective tube 40. If the area of the lumen at the one end of the protective tube 40 is larger than the area of the lumen at the midpoint P1 of the length in the distal-proximal direction of the protective tube 40, the protective tube 40 is less likely to squeeze the projecting portion 30 disposed at the one end of the balloon 20. In addition, if the area of the lumen at the one end of the protective tube 40 is larger than the area of the lumen at the midpoint P1 of the length in the distal-proximal direction of the protective tube 40, it becomes easy to dispose the balloon 20 in the lumen of the protective tube 40 by inserting the balloon 20 from the one end of the protective tube 40.

The area of the lumen in the cross section perpendicular to the distal-proximal direction of the protective tube 40 at the one end of the protective tube 40 is preferably not smaller than 1.05 times, more preferably not smaller than 1.1 times, and further preferably not smaller than 1.15 times the area of the lumen in the cross section perpendicular to the distal-proximal direction of the protective tube 40 at the midpoint P1 of the length in the distal-proximal direction of the protective tube 40. If the lower limit value of the ratio of the area of the lumen at the one end of the protective tube 40 to the area of the lumen at the midpoint P1 of the length in the distal-proximal direction of the protective tube 40 is set to fall within the above range, the projecting portion 30 disposed at the one end of the balloon 20 can be prevented from being squeezed by the protective tube 40, and the projecting portion 30 can be prevented from being flattened. Meanwhile, the area of the lumen in the cross section perpendicular to the distal-proximal direction of the protective tube 40 at the one end of the protective tube 40 is preferably not larger than 3 times, more preferably not larger than 2.5 times, and further preferably not larger than 2 times the area of the lumen in the cross section perpendicular to the distal-proximal direction of the protective tube 40 at the midpoint P1 of the length in the distal-proximal direction of the protective tube 40. If the upper limit value of the ratio of the area of the lumen at the one end of the protective tube 40 to the area of the lumen at the midpoint P1 of the length in the distal-proximal direction of the protective tube 40 is set to fall within the above range, the area of the lumen at the one end of the protective tube 40 is prevented from being excessively increased. As a result, the balloon 20 disposed at the one end of the protective tube 40 is less likely to swell during an air leak test of the balloon 20.

It is preferable that the area of the lumen in a cross section perpendicular to the distal-proximal direction of the protective tube 40 is larger at least at one end of the protective tube 40 than at the midpoint P1 of the length in the distal-proximal direction of the protective tube 40. It is more preferable that the area of the lumen at one end of the protective tube 40 and the area of the lumen at another end of the protective tube 40 are larger than the area of the lumen at the midpoint P1 of the length in the distal-proximal direction of the protective tube 40. That is, it is more preferable that the area of the lumen in a cross section perpendicular to the distal-proximal direction of the protective tube 40 at each of both ends of the protective tube 40 is larger than the area of the lumen in the cross section perpendicular to the distal-proximal direction of the protective tube 40 at the midpoint P1 of the length in the distal-proximal direction of the protective tube 40. If the area of the lumen at each of both ends of the protective tube 40 is larger than the area of the lumen at the midpoint P1 of the length in the distal-proximal direction of the protective tube 40, the one end and the other end of the protective tube 40 do not need to be distinguished from each other at the time of disposing the balloon 20 in the lumen of the protective tube 40. Thus, production efficiency for the balloon catheter 1 can be increased.

FIG. 4 is a cross-sectional view, at IV-IV, of the balloon catheter 1 shown in FIG. 1. FIG. 4 is a cross-sectional view perpendicular to the distal-proximal direction at one end of the protective tube 40. As shown in FIGS. 3A and 3B and FIG. 4, it is preferable that: a cross-sectional shape, of the lumen of the protective tube 40, perpendicular to the distal-proximal direction at each of the midpoint P1 of the length in the distal-proximal direction of the protective tube 40 and the one end of the protective tube 40, is a polygon; and the number of corners of the polygon which is the cross-sectional shape, of the lumen of the protective tube 40, perpendicular to the distal-proximal direction at the midpoint P1 of the length in the distal-proximal direction of the protective tube 40 is smaller than the number of corners of the polygon which is the cross-sectional shape, of the lumen of the protective tube 40, perpendicular to the distal-proximal direction at the one end of the protective tube 40. If the number of the corners of the polygon which is the cross-sectional shape, of the lumen of the protective tube 40, perpendicular to the distal-proximal direction at the midpoint P1 of the length in the distal-proximal direction of the protective tube 40 is smaller than the number of the corners of the polygon which is the cross-sectional shape, of the lumen of the protective tube 40, perpendicular to the distal-proximal direction at the one end of the protective tube 40, the cross-sectional shape of the lumen at the one end of the protective tube 40 has a larger number of corners and has a shape more similar to a circle, than the cross-sectional shape of the lumen at the midpoint P1 of the length in the distal-proximal direction of the protective tube 40. That is, the cross-sectional shape of the lumen at the one end, of the protective tube 40, which serves as an insertion port for the balloon 20 at the time of disposing the balloon 20 in the lumen of the protective tube 40, is similar to a circle. Thus, the insertion port is wide, and the balloon 20 is easily inserted into the lumen of the protective tube 40. Therefore, since the cross-sectional shape of the lumen at the midpoint P1 of the length in the distal-proximal direction of the protective tube 40 has a smaller number of corners than the cross-sectional shape of the lumen at the one end of the protective tube 40, the gap generated between the inner surface of the protective tube 40 and the outer surface of the balloon 20 is small, whereby the balloon 20 can be made less likely to swell in the protective tube 40 during an air leak test of the balloon 20.

It is preferable that: the number of the projecting portions 30 is more than one; the number of the corners of the polygon which is the cross-sectional shape, of the lumen of the protective tube 40, perpendicular to the distal-proximal direction at the midpoint P1 of the length in the distal-proximal direction of the protective tube 40 is equal to the number of the projecting portions 30; and the number of the corners of the polygon which is the cross-sectional shape, of the lumen of the protective tube 40, perpendicular to the distal-proximal direction at the one end of the protective tube 40 is 2 times the number of the projecting portions 30. If the number of the corners of the polygon which is the cross-sectional shape, of the lumen of the protective tube 40, perpendicular to the distal-proximal direction at the midpoint P1 of the length in the distal-proximal direction of the protective tube 40 is equal to the number of the projecting portions 30 and the number of the corners of the polygon which is the cross-sectional shape, of the lumen of the protective tube 40, perpendicular to the distal-proximal direction at the one end of the protective tube 40 is 2 times the number of the projecting portions 30, the gap between the inner surface of the protective tube 40 and the outer surface of the balloon 20 is small at the midpoint P1 of the length in the distal-proximal direction of the protective tube 40 and the size of the insertion port for the balloon 20 can be sufficiently increased at the one end of the protective tube 40. Therefore, while the balloon 20 is easily inserted into the protective tube 40, the balloon 20 can be prevented from significantly swelling in the protective tube 40 during an air leak test of the balloon 20.

FIG. 5 is a cross-sectional view perpendicular to the distal-proximal direction at the one end of the protective tube 40 in another embodiment. As shown in FIG. 5, it is also preferable that the cross-sectional shape, of the lumen of the protective tube 40, perpendicular to the distal-proximal direction at the one end of the protective tube 40 is a circle or an ellipse. If the cross-sectional shape, of the lumen of the protective tube 40, perpendicular to the distal-proximal direction at the one end of the protective tube 40 is a circle or an ellipse, the cross-sectional shape of the lumen at the one end, of the protective tube 40, which serves as the insertion port for the balloon 20 can be ensured to have a large area. As a result, the balloon 20 can be easily inserted into the lumen of the protective tube 40.

In a case where the cross-sectional shape, of the lumen of the protective tube 40, perpendicular to the distal-proximal direction at the one end of the protective tube 40 is a circle or an ellipse, the cross-sectional shape, of the lumen of the protective tube 40, perpendicular to the distal-proximal direction at the midpoint P1 of the length in the distal-proximal direction of the protective tube 40 is preferably a polygon having the same number of corners as the number of the projecting portions 30. If the cross-sectional shape, of the lumen of the protective tube 40, perpendicular to the distal-proximal direction at the midpoint P1 of the length in the distal-proximal direction of the protective tube 40 is a polygon having the same number of corners as the number of the projecting portions 30 and the cross-sectional shape, of the lumen of the protective tube 40, perpendicular to the distal-proximal direction at the one end of the protective tube 40 is a circle or an ellipse, a large gap is less likely to be generated between the inner surface of the protective tube 40 and the outer surface of the balloon 20 at the midpoint P1 of the length in the distal-proximal direction of the protective tube 40, and the insertion port for the balloon 20 is wide and it becomes easy to insert the balloon 20 into the lumen of the protective tube 40 at the one end of the protective tube 40.

Although not shown, the protective tube 40 includes a transitional portion between the midpoint P1 of the length in the distal-proximal direction of the protective tube 40 and the one end of the protective tube 40. The transitional portion is preferably such that the shape of the lumen at the transitional portion is helically twisted about the distal-proximal direction. Since the protective tube 40 includes the transitional portion between the midpoint P1 of the length in the distal-proximal direction of the protective tube 40 and the one end of the protective tube 40, the shape of the inside of the protective tube 40 can be smoothly deformed even when the shape of the lumen of the protective tube 40 is different between the midpoint P1 of the length in the distal-proximal direction of the protective tube 40 and the one end of the protective tube 40. Therefore, when the balloon 20 is disposed in the protective tube 40, the inner surface of the protective tube 40 and the outer surface of the balloon 20 are less likely to interfere with each other, and the balloon 20 can be easily inserted into the lumen of the protective tube 40.

FIG. 6 is a cross-sectional view perpendicular to the distal-proximal direction at the midpoint P1 of the length in the distal-proximal direction of the protective tube 40 in still another embodiment of the present invention. As shown in FIG. 6, it is preferable that, in the cross section perpendicular to the distal-proximal direction: the number of the projecting portions 30 is more than one; and each wing-shaped portion 21 has an origin 22 located closer to one side relative to a straight line L1 connecting the centroid P2 of the protective tube 40 to a midpoint P3 between the apex 31 of a projecting portion 30 and the apex 31 of a projecting portion 30 adjacent to the projecting portion 30 among the projecting portions 30. If each wing-shaped portion 21 has the origin 22 located closer to one side relative to the straight line L1 connecting the centroid P2 of the protective tube 40 to the midpoint P3 between the apex 31 of a projecting portion 30 and the apex 31 of a projecting portion 30 adjacent to the projecting portion 30 among the projecting portions 30, the origin 22 of the wing-shaped portion 21 is located closer to one projecting portion 30 out of the projecting portion 30 on the one side and the projecting portion 30 on the other side adjacent to the projecting portion 30 on the one side. That is, the origin 22 is located closer to the one side relative to the midpoint P3. Consequently, the wing-shaped portion 21 can be folded and housed in a space that is closer to the other side relative to the midpoint P3. Thus, the wing-shaped portion 21 is easily housed in a space from the origin 22 of the wing-shaped portion 21 to the projecting portion 30 on the other side in an orderly manner, and the gap generated between the inner surface of the protective tube 40 and the outer surface of the balloon 20 is made small. Therefore, the balloon 20 can be made less likely to swell in the protective tube 40 during an air leak test of the balloon 20.

As shown in FIG. 6, it is preferable that, in the cross section perpendicular to the distal-proximal direction, the wing-shaped portion 21 has a tip 23 located closer to another side opposite to the one side. That is, it is preferable that, in the cross section perpendicular to the distal-proximal direction: each wing-shaped portion 21 has the origin 22 located closer to the one side relative to the straight line L1 connecting the centroid P2 of the protective tube 40 to the midpoint P3 between the apex 31 of a projecting portion 30 and the apex 31 of a projecting portion 30 adjacent to the projecting portion 30 among the projecting portions 30; and the wing-shaped portion 21 has the tip 23 closer to the other side. If each wing-shaped portion 21 has the origin 22 located closer to the one side relative to the straight line L1 connecting the centroid P2 of the protective tube 40 to the midpoint P3 between the apex 31 of a projecting portion 30 and the apex 31 of a projecting portion 30 adjacent to the projecting portion 30 among the projecting portions 30 and the wing-shaped portion 21 has the tip 23 closer to the other side, the distance between the origin 22 and the tip 23 of the wing-shaped portion 21 can be elongated in a space between the projecting portions 30 that are adjacent to each other. Therefore, the balloon 20 can be easily housed in the protective tube 40.

FIG. 7 is a cross-sectional view perpendicular to the distal-proximal direction at the midpoint P1 of the length in the distal-proximal direction of the protective tube 40 in a different embodiment of the present invention. As shown in FIG. 7, it is more preferable that, in the cross section perpendicular to the distal-proximal direction: the wing-shaped portion 21 has the origin 22 located closer to the one side relative to a point P5 on the one side out of points that equally trisect the distance between the two adjacent projecting portions 30; and the wing-shaped portion 21 has the tip 23 closer to the other side relative to a point P6 on the other side out of the points. If the origin 22 of the wing-shaped portion 21 is located closer to the one side relative to the point P5 on the one side out of the points that equally trisect the distance between the two adjacent projecting portions 30 and the tip 23 of the wing-shaped portion 21 is located closer to the other side relative to the point P6 on the other side out of the points that equally trisect the distance between the two adjacent projecting portions 30, the wing-shaped portion 21 can be folded and housed in a space, between the two adjacent projecting portions 30, in which the origin 22 of the wing-shaped portion 21 is not present. Thus, the wing-shaped portion 21 can be housed in an orderly state in the space from the origin 22 of the wing-shaped portion 21 to the projecting portion 30 that is more apart from the origin 22 of the wing-shaped portion 21. Therefore, the balloon 20 can be easily housed in the lumen of the protective tube 40.

As shown in FIGS. 3A and 3B, FIG. 6, and FIG. 7, it is preferable that: the wing-shaped portions 21 are wound and folded in the circumferential direction of the balloon 20; and all the wing-shaped portions 21 are folded in one direction of the circumferential direction of the balloon 20. That is, all the wing-shaped portions 21 are preferably wound and folded in the same direction. If all the wing-shaped portions 21 are folded in one direction of the circumferential direction of the balloon 20, the wing-shaped portions 21 can be folded in an orderly manner. As a result, it becomes easy to insert the balloon 20 into the protective tube 40.

As shown in FIGS. 3A and 3B and FIG. 6, it is preferable that the projecting portions 30 include a projecting portion 30 that has an apex 31 in contact with a corresponding one of the wing-shaped portions 21. In addition, it is more preferable that the apexes 31 of all the projecting portions 30 are in contact with the wing-shaped portions 21. If the projecting portions 30 include the projecting portion 30 that has the apex 31 in contact with the corresponding wing-shaped portion 21, the wing-shaped portion 21 can be held by the inner surface of the protective tube 40 and the apex 31 of the projecting portion 30. Therefore, in the lumen of the protective tube 40, the wing-shaped portion 21 can be prevented from moving, and the wing-shaped portion 21 of the balloon 20 can be prevented from significantly swelling during an air leak test of the balloon 20.

In addition, as shown in FIG. 7, it is also preferable that the projecting portions 30 include a projecting portion 30 that has an apex 31 in contact with the inner surface of the protective tube 40. Further, it is more preferable that the apexes 31 of all the projecting portions 30 are in contact with the inner surface of the protective tube 40. If the projecting portions 30 include a projecting portion 30 that has an apex 31 in contact with the inner surface of the protective tube 40, a gap is less likely to be generated between the inner surface of the protective tube 40 and the outer surface of the balloon 20 when the balloon 20 is disposed in the lumen of the protective tube 40. As a result, the balloon 20 can be made less likely to swell in the protective tube 40 during an air leak test of the balloon 20.

Although not shown, an X-ray opaque marker may be disposed at a portion, of the shaft 10, on which the balloon 20 is located. If the X-ray opaque marker is disposed at the portion, of the shaft 10, on which the balloon 20 is located, the location of the balloon 20 can be confirmed during an X-ray fluoroscopy, and the location at which the balloon 20 is present in the body can be easily confirmed.

The X-ray opaque marker is preferably disposed on the shaft 10 at each of portions located on the distal end and the proximal end of the balloon 20. If the X-ray opaque marker is disposed at each of the portions located on the distal end and the proximal end of the balloon 20, the locations of both the distal end and the proximal end of the balloon 20 can be confirmed during an X-ray fluoroscopy, and the location of the balloon 20 in the body can be ascertained.

As the material of the X-ray opaque marker, for example, an X-ray opaque substance such as lead, barium, iodine, tungsten, gold, platinum, iridium, stainless steel, titanium, or a cobalt-chromium alloy can be used. In particular, the X-ray opaque substance is preferably platinum. If the material of the X-ray opaque marker is platinum, X-ray imaging performance can be increased, and the location of the balloon 20 is easily confirmed.

Examples of the shape of the X-ray opaque marker include a cylindrical shape, a polygonal tubular shape, a shape having a C-shaped cross section obtained by cutting a tube, the shape of a coil obtained by winding a wire, and the like. In particular, the shape of the X-ray opaque marker is preferably a cylindrical shape. If the shape of the X-ray opaque marker is a cylindrical shape, the visibility of the X-ray opaque marker during an X-ray fluoroscopy can be increased, and the location of the balloon 20 in the body can be swiftly confirmed.

As described above, the balloon catheter includes: a shaft extending in a distal-proximal direction; a balloon disposed on a distal side of the shaft and having, in a contracted state, a plurality of wing-shaped portions; projecting portions disposed on an outer surface of the balloon; and a protective tube having a lumen in which the balloon is disposed, wherein, in a cross section perpendicular to the distal-proximal direction at a midpoint of a length in the distal-proximal direction of the protective tube, a distance from a centroid of the protective tube through an apex of each projecting portion to an inner surface of the protective tube is longer than a distance from the centroid of the protective tube through none of the projecting portions to the inner surface of the protective tube in an interval between the projecting portion and an adjacent projecting portion among the projecting portions. Since, in the cross section perpendicular to the distal-proximal direction at the midpoint of the length in the distal-proximal direction of the protective tube, the distance from the centroid of the protective tube through the apex of each projecting portion to the inner surface of the protective tube is longer than the distance from the centroid of the protective tube through none of the projecting portions to the inner surface of the protective tube in the interval between the projecting portion and the adjacent projecting portion, the gap between the protective tube and the balloon is made small in a state where the balloon is housed in the lumen of the protective tube, the balloon is less likely to swell in the protective tube during an air leak test of the balloon, and the balloon having the projecting portions can be easily housed in the lumen of the protective tube.

The present application claims the benefit of priority based on Japanese patent application number 2019-063580 filed on Mar. 28, 2019. The entire content of the specification of Japanese patent application number 2019-063580 filed on Mar. 28, 2019 is incorporated herein by reference.

DESCRIPTION OF REFERENCE SIGNS 1 balloon catheter
2 hub
3 fluid injection portion
4 guide wire insertion portion
10 shaft
11 inner tube
20 balloon
21 wing-shaped portion
22 origin
23 tip
30 projecting portion
31 apex
40 protective tube
P1 a midpoint of the length in the distal-proximal direction of the protective tube
P2 centroid of the protective tube
P3 midpoint between the apex of a projecting portion and the apex of a projecting portion adjacent to the projecting portion among the projecting portions
P5 point on the one side out of points that equally trisect the distance between the two adjacent projecting portions
P6 point on the other side out of the points that equally trisect the distance between the two adjacent projecting portions
D1 distance from a centroid of the protective tube through the apex of each projecting portion to the inner surface of the protective tube
D2 distance from the centroid of the protective tube through none of the projecting portions to the inner surface of the protective tube
L1 line connecting the midpoint P3 and the centroid P2 of the protective tube

The invention claimed is:

1. A balloon catheter comprising:
a shaft extending in a distal-proximal direction;
a balloon disposed on a distal side of the shaft and having, in a contracted state, a plurality of wing-shaped portions;
projecting portions disposed on an outer surface of the balloon;
a protective tube having a lumen in which the balloon is disposed, wherein, in a cross section perpendicular to the distal-proximal direction at a midpoint of a length in the distal-proximal direction of the protective tube, D1 is longer than D2, where D1 is a distance from a centroid of the protective tube through an apex of each projecting portion to an inner surface of the protective tube, and D2 is a distance from the centroid of the protective tube to the inner surface of the protective tube through none of the projecting portions and a portion between the projecting portions adjacent to each other; and wherein the balloon in the contracted state is disposed in the protective tube so that, in the cross section perpendicular to the distal-proximal direction at the midpoint of the length in the distal-proximal direction of the protective tube, 50% or less of an outer surface area of the balloon facing the inner surface of the protective tube contacts with the inner surface of the protective tube.

2. The balloon catheter according to claim 1, wherein D1 is not smaller than 1.1 times and not larger than 4.0 times D2.

3. The balloon catheter according to claim 1, wherein a cross-sectional shape, of the lumen of the protective tube, perpendicular to the distal-proximal direction at the midpoint of the length in the distal-proximal direction of the protective tube is a polygon.

4. The balloon catheter according to claim 3, wherein a cross-sectional shape of the lumen of the protective tube perpendicular to the distal-proximal direction at one end of the protective tube is a polygon, and the number of corners of the polygon of the lumen of the protective tube in a cross section perpendicular to the distal-proximal direction at the midpoint of the length in the distal-proximal direction of the protective tube is smaller than the number of corners of the polygon of the lumen of the protective tube in a cross section perpendicular to the distal-proximal direction at the one end of the protective tube.

5. The balloon catheter according to claim 3, wherein the number of corners of the polygon is a multiple of the number of the projecting portions.

6. The balloon catheter according to claim 5, wherein the number of the corners of the polygon is equal to the number of the projecting portions.

7. The balloon catheter according to claim 5, wherein the projecting portions are disposed at the corners of the polygon.

8. The balloon catheter according to claim 6, wherein the projecting portions are disposed at the corners of the polygon.

9. The balloon catheter according to claim 1, wherein, in the cross section perpendicular to the distal-proximal direction at the midpoint of the length in the distal-proximal direction of the protective tube, an area of the balloon obtained by subtracting a cross-sectional area of each projecting portion from a total cross-sectional area of the balloon is not lower than 20% of an area obtained by subtracting the cross-sectional area of the projecting portion from a cross-sectional area of the lumen of the protective tube.

10. The balloon catheter according to claim 1, wherein, in the cross section perpendicular to the distal-proximal direction at the midpoint of the length in the distal-proximal direction of the protective tube, a proportion of an outer periphery, of the balloon, that is in contact with the inner surface of the protective tube to an entire outer periphery of the balloon is not lower than 20%.

11. The balloon catheter according to claim 1, further comprising an inner tube which is located in a lumen of the balloon and through which a guide wire is inserted, and in the cross section perpendicular to the distal-proximal direction at the midpoint of the length in the distal-proximal direction of the protective tube, an area obtained by subtracting a cross-sectional area of each projecting portion from a total cross-sectional area of the balloon is not lower than 20% of an area obtained by subtracting the cross-sectional area of the projecting portion from a cross-sectional area of a space between the inner surface of the protective tube and an outer surface of the inner tube.

12. The balloon catheter according to claim 1, wherein the balloon and the projecting portions are made as an integrally molded product.

13. The balloon catheter according to claim 1, wherein a cross-sectional area of the lumen in a cross section perpendicular to the distal-proximal direction of the protective tube at one end of the protective tube is larger than a cross-sectional area of the lumen in the cross section perpendicular to the distal-proximal direction of the protective tube at the midpoint of the length in the distal-proximal direction of the protective tube.

14. The balloon catheter according to claim 1, wherein a cross-sectional shape of the lumen of the protective tube, in a cross section perpendicular to the distal-proximal direction at one end of the protective tube, is a circle or an ellipse.

15. The balloon catheter according to claim 1, wherein the protective tube includes a transitional portion between the midpoint of the length in the distal-proximal direction of the protective tube and one end of the protective tube, and the transitional portion is disposed in the protective tube such that a shape of the lumen at the transitional portion is helically twisted about the distal-proximal direction.

16. The balloon catheter according to claim 1, wherein in the cross section perpendicular to the distal-proximal direction, each wing-shaped portion is connected to the balloon at a position, which is located at either side relative to an imaginative straight line connecting from the centroid of the protective tube to a midpoint between the apexes of the projecting portions adjacent to the wing-shaped portion.

17. The balloon catheter according to claim 16, wherein, in the cross section perpendicular to the distal-proximal direction, the wing-shaped portion is fold such that a tip of the wing-shaped portion is located at a different side, with respect to the imaginative straight line, from the side at which the wing-shaped portion is connected to the balloon.

18. The balloon catheter according to claim 1, wherein
the wing-shaped portions are wound and folded in a circumferential direction of the balloon, and
all the wing-shaped portions are folded in one direction of the circumferential direction of the balloon.

19. The balloon catheter according to claim 1, wherein an apex of at least one projecting portion of the projecting portions contacts with one of the wing-shaped portions.

20. The balloon catheter according to claim 1, wherein an apex of at least one projecting portion of the projecting portions contacts with the inner surface of the protective tube.

* * * * *